(12) United States Patent
Meudt et al.

(10) Patent No.: US 8,487,134 B2
(45) Date of Patent: Jul. 16, 2013

(54) PROCESS FOR THE SYNTHESIS OF AMPHETAMINE DERIVATIVES

(75) Inventors: Andreas Meudt, Hofheim (DE); Richard Wisdom, Eppstein (DE); Jason Helmke, Rogersville, MO (US); Quofang Qiu, Springfield, MO (US); Paul Meek, Republic, MO (US)

(73) Assignee: Archimica, Inc., Springfield, MO (US)

( * ) Notice: Subject to any disclaimer, the term of this patent is extended or adjusted under 35 U.S.C. 154(b) by 192 days.

(21) Appl. No.: 13/122,893

(22) PCT Filed: Oct. 9, 2008

(86) PCT No.: PCT/US2008/079356
§ 371 (c)(1),
(2), (4) Date: Apr. 6, 2011

(87) PCT Pub. No.: WO2010/042120
PCT Pub. Date: Apr. 15, 2010

(65) Prior Publication Data
US 2011/0196173 A1    Aug. 11, 2011

(51) Int. Cl.
*C07C 233/05*    (2006.01)
*C07C 231/02*    (2006.01)

(52) U.S. Cl.
USPC ............................. 564/194; 564/138; 564/139

(58) Field of Classification Search
USPC ........................................ 564/138, 139, 194
See application file for complete search history.

(56) References Cited

FOREIGN PATENT DOCUMENTS
WO    WO 2006/121552 A2    11/2006

OTHER PUBLICATIONS

ARCHIMICA Coupling Agnet T3P—The Water Scavenger: High-Performance Amide/Peptide Bond Formations, Dehydrations and Condensations. ARCHIMICA brochure, Oct. 2006, pp. 1-20.

*Primary Examiner* — Shailendra Kumar
(74) *Attorney, Agent, or Firm* — ProPat, L.L.C.

(57) ABSTRACT

The invention relates to processes for preparing acylated amphetamine, methamphetamine and dexamphetamine derivatives by reacting the parent amine with the to be-coupled acid or a salt of the to-be coupled acid which acid is optionally protected, in the presence of an alkylphosphonic acid anhydride as coupling agent and, if the acid was protected then cleaving the protecting group(s), in a one-pot reaction or in two or more separate steps.

12 Claims, No Drawings

PROCESS FOR THE SYNTHESIS OF AMPHETAMINE DERIVATIVES

CROSS-REFERENCE TO RELATED APPLICATIONS

This application is being filed under Rule 1.371 as a National Stage Application of pending International Application No. PCT/US2008/079356 filed Oct. 9, 2008, and claims priority thereto. International Application No. PCT/EP2008/079356 is hereby incorporated by reference herein in its entirety.

FIELD OF THE INVENTION

The present invention relates to methods for manufacturing amphetamine derivatives, particularly to methods for manufacturing amphetamine derivatives using an amphetamine coupling reaction.

BACKGROUND OF THE INVENTION

Amphetamine and related drugs have highly important pharmaceutical properties and are used in a variety of applications. These compounds act by increasing levels of norepinephrine, serotonin, and dopamine in the brain. Some of the medical indications are (a) CNS drugs commonly used to treat attention-deficit disorder (ADD) and attention-deficit hyperactivity disorder (ADHD) in adults and children and (b) to treat symptoms of traumatic brain injury and the daytime drowsiness symptoms of narcolepsy and chronic fatigue syndrome. Just to mention a few drugs that contain Amphetamine and derivatives, Vyvanse, Adderall, and Dexedrine belong to this family of drugs.

Due to the major importance of Amphetamine derivatives, numerous synthetic methods for their synthesis and their derivatisation have been developed (e.g. patent WO/2006/121552). A general problem which has to be overcome is the fact that Amphetamines include a stereodefined amine center which is potentially subject to racemisation. As a result, only methods which suppress racemisation can be applied. At the same time, these methods do need to fulfil the standard economic requirements of high yields, high selectivity and low process costs. Typically such reactions involve a coupling agent. Due to the production application area, coupling reagents also need to be non-toxic to avoid any risk.

For the synthesis and derivatisation of most Amphetamine derivatives, a variety of different coupling reagents has been tested but so far none has fulfilled all of the above requirements.

SUMMARY OF ADVANTAGEOUS EMBODIMENTS OF THE INVENTION

It was, therefore, an object of the present invention to provide for a method to manufacture amphetamine derivatives using an amphetamine coupling reaction which
- avoids racemisation of the stereodefined amphetamine amine centre, i.e. the degree of racemisation is typically less than 1.0%, preferably less than 0.5%, more preferably less than 0.2%
- has a yield of 90% and higher, preferably higher than 95%, more preferably higher than 98%
- is of low complexity with regards to coupling process and workup and
- uses a non-toxic coupling agent.

More specifically it was an object of the present invention to provide for a process for the derivatisation of Amphetamines, Dexamphetamines and Methamphetamines in coupling reactions to acylated products in high yields and without racemisation, in easy processes.

The present invention achieves these objects. Surprisingly, it was found that the application of alkyl phosphonic acid anhydrides, especially cyclic anhydrides, e.g. T3P®, in the coupling reaction leads to an almost quantitative conversion of Amphetamines to coupled products, without any detectable racemisation.

DETAILED DESCRIPTION OF ADVANTAGEOUS EMBODIMENTS OF THE INVENTION

Accordingly, the present invention relates to a process for preparing acylated amphetamine, methamphetamine and dexamphetamine derivatives including their salts by reacting the parent amine with the optionally protected to be coupled acid or a salt of the to be coupled acid in the presence of an alkylphosphonic acid anhydride as coupling agent and, if required, the cleavage of the protecting group(s), in a one-pot reaction or in two or more separate steps. The reaction is illustrated in the following equation 1.

EQUATION 1

$$R_1\text{-}C(R_2)(R_3)\text{-}NH \quad \text{or} \quad R_1\text{-}C(R_2)(R_3)\text{-}NH + HO\text{-}C(=O)\text{-}R_4 + \left[\begin{array}{c} O \\ \| \\ \text{-P-O-} \\ | \\ R_5 \end{array}\right]_n \longrightarrow$$

$$R_1\text{-}C(R_2)(R_3)\text{-}N(R_4)\text{-}C(=O) \quad \text{or} \quad R_1\text{-}C(R_2)(R_3)\text{-}N(R_4)\text{-}C(=O) \xrightarrow[\text{deprotection}]{\text{optional}} \left[\begin{array}{c}\text{deprotected} \\ \text{Amphetamine} \\ \text{derivative}\end{array}\right]$$

In the above equation 1, n and the radicals R1 to R5 have the following meaning:

R1 is benzyl, mono-, di-, tri-lower-alkyl-substituted phenylmethyl, mono-, di- or tri-lower-alkoxy-substituted phenylmethyl.

R2 is lower alkyl

R3 is H or lower alkyl

R4 is an amino acid radical or an amino acid radical wherein at least one amino group is protected with a protecting group, or is a substituted alkyl group different from an amino acid radical R5 is C1-C8-alkyl n is a number ranging from 3 to 5 (in case of cyclic anhydrides) or 3 to 1000 (in case of open-chain oligomers), including mixtures of different open-chain and/or cyclic anhydrides.

Preferably n and the radicals R1 to R5 have the following meaning:

R1 is benzyl, o-, m-, p-tolyl, o-, m-, p-anisyl

R2 is methyl

R3 is H, methyl, ethyl.

R4 is an amino acid radical or an amino acid radical wherein at least one amino group is protected with a protecting group R5 is methyl, ethyl, i-propyl, n-propyl, and n 3 (in case of cyclic anhydrides) and 3 to 700 (in case of open-chain oligomers), including mixtures of different open-chain and/or cyclic anhydrides More preferably n and the radicals R1 to R5 have the following meaning:

R1=benzyl,

R2=methyl,

R3=H or methyl,

R4=PG-NH—$(CH_2)_4$—CH(NH-PG),

R5=i-propyl, n-propyl, and n=3 (in case of cyclic anhydrides) and 3 to 500 (in case of open-chain oligomers), including mixtures of different open-chain and/or cyclic anhydrides.

"Alkyl" in general means any n-alkyl or i-alkyl or sec-alkyl or tert.-alkyl group with the given number of carbon atoms.

"Substituted alkyl group" is a C1-C12-alkyl group which is mono- or di- or multiple-substituted with one or more groups selected from $NH_2$, $NO_2$, OH, SH, COOH, CHO, CN, OCN, $SO_3H$, $SO_3Na$, $SO_2$, Cl, Br, I, phenyl, pyridyl, pyrollyl etc.

"Lower alkyl" means straight chain or branched $C_1$-$C_4$-alkyl; preferably methyl, ethyl or propyl.

"Amino acid radical" means the de-carboxy part of a (natural) amino acid selected from the group consisting of glycine, alanine, valine, leucine, isoleucine, cysteine, methionine, phenylalanine, tyrosine, tryptophane, proline, serine, threonine, asparagine, glutamine, aspartic acid, glutamic acid, histidine, lysine and arginine.

"PG" or "Protecting Group" means any group known to those skilled in the art that can be used to reversibly block an amine; e.g. 9-fluorenylmethyl carbamate (Fmoc), t-butyl carbamate (Boc), benzyl carbamate (Z. Cbz) acetamide (Ac), trifluoroacetamide, phthalimide, benzylamine (Bn), triphenylmethylamine (Tr), benzylideneamine, p-toluenesulfonamide (Ts), pivaloyl (Piv), etc.

The alkylphosphonic acid anhydride of the formula $$\left[\begin{array}{c} O \\ \parallel \\ P-O \\ | \\ R_5 \end{array}\right]_n$$

is either cyclic (see formula I below) or linear (see formula II below). If it is linear the open bonds are saturated by OH and H respectively (see formula II below).

An example of the process according to the invention is the synthesis of Lisdexamphetamine (VI), a prodrug for d-Amphetamine, by coupling of protected Lysine (IV, PG=Protective Group, e.g. Boc) with d-Amphetamine (III), followed by deprotection (equation 2).

EQUATION 2

III + IV → V → VI

A variety of different alkylphosphonic acid anhydrides can be used. They can be cyclic or linear. In both cases the alkyl substituent can be the same or different per molecule. Preferably the cyclic anhydride is a trimer, specifically of iso- and/or n-propylphosphonic acid anhydride or is an open-chain oligo- or polymer or is a mixture of such cyclic and open-chain compounds; most preferably it is the anhydride of n-propane (and some iso-propane) phosphonic acid, which primarily consists of the cyclic trimer. This most preferred anhydride is commercially available as T3P® from Archimica GmbH, Frankfurt, Germany (Formula I, R=n-propyl (with some iso-propyl)). The surprising advantages of T3P, and the other phosphonic acid anhydrides in the reaction according to the invention are their very high selectivities, leading to highest yields and product purities and to the lowest level of racemisation and epimerisation. These alkylphosphonic acid anhydrides are non-toxic and very easy to process, resulting in an overall reduction of process costs. Workup can be performed by a simple hydrolysis and phase separation, which results in a—surprisingly already very pure—product solution in an organic solvent and a phosphorous product in the aqueous phase.

I

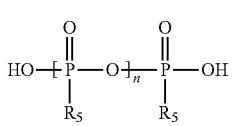

The anhydride can be used as a pure material, but typically it is applied as a solution in an organic solvent for reasons of most economic processes. A solvent can be selected from those available materials which do not react with the phosphonic acid anhydride, especially aprotic organic solvents. Possible solvents are Ligroine, Pentane, Hexane, Heptane, Octane, Cyclopentane, Cyclohexane, Cycloheptane, Cyclooctane, Dichloromethane, Chloroform, Carbon tetrachloride, 1,2-Dichloroethane, 1,1,2,2-Tetrachloroethane, Methylacetate, Ethylacetate, Propylacetate, Butylacetate, Dimethylformamide, Diethylformamide, Dimethylacetamide, Diethylacetamide, Diethylether, Diisopropylether, tert.-Butyl-methylether, THF, Dioxane, Acetonitrile, Sulfolan, DMSO, HMPT, NMP or mixtures of these solvents. Preferred solvents are Dichloromethane, Chloroform, Ethylacetate, Propylacetate, Butylacetate, Dimethylformamide, Diethylformamide, Dimethylacetamide, Diethylacetamide, Diisopropylether, tert.-Butyl-methylether, THF, Dioxane, Acetonitrile or mixtures of these. Especially preferred solvents are Dichloromethane, Chloroform, Ethylacetate, Butylacetate, Dimethylformamide, Dimethylacetamide, tert.-Butyl-methylether, THF, Dioxane, Acetonitrile or mixtures of these.

The coupling reactions are preferably performed at temperatures in the range of −20° C. to +80° C., especially between −5° C. and +30° C.

Different coupling strategies can be applied. A standard method comprises mixing the substrates (Amphetamine derivative, acid, base and solvent) and slowly adding a phosphonic acid anhydride solution to this mixture. After completion of the addition, the mixture is stirred for some time, e.g. for another hour, followed by hydrolysis of the mixture (to quench the catalyst), phase separation, and if required further extractions and/or pH adjustments. The coupling step can be conducted as a one-pot reaction.

The reaction is preferably performed in the presence of a base. As bases, both organic (amines) or inorganic bases can be used (hydrogen carbonates, carbonates, hydroxides, etc.). Best results are typically achieved with using 1-3 equivalents of base plus one additional equivalent for each acid equivalent present in the substrates (e.g. hydrochloride)

Despite the extremely high selectivities of T3P and other phosphonic acid anhydrides, protection strategies are often needed if there are different amine or acid functionalities with comparable reactivity. In the case of Lisdexamphetamine, the protection of the two amino groups of Lysine can be accomplished with Boc groups which result in high overall yields and very easy cleavage after the coupling to yield Lisdexamphetamine as a free base or as a salt.

Surprisingly, the coupling reaction according to the invention leads to almost quantitative conversion of Amphetamines with a yield >90%, preferably >95%, more preferably >98% to coupled products at very high purities (>98.0%, preferably >99.0%, more preferably >99.5%), without any detectable racemisation (ee loss <1.0%, preferably <0.5, more preferably <0.2).

The process of the invention is illustrated by the following examples:

Example 1

Synthesis of L-lysine-d-amphetamine dimesylate

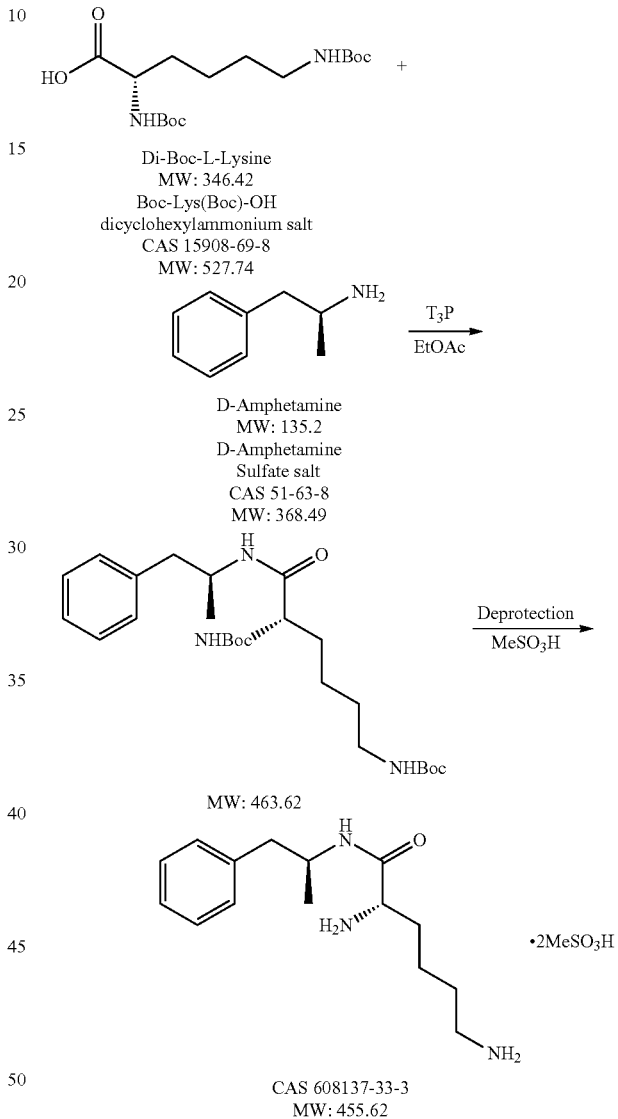

L-Lysine-d-Amphetamine Dimesylate was Synthesized by T3P Coupling of Di-Boc-L-Lysine Free Acid with D-Amphetamine Free Base Preparation of the Free Acid of Di-N-Boc-L-Lysine:

Di-N-Boc-L-Lysine dicyclohexylammonium salt (2.0 g, 3.8 mmol) was taken up with 75 ml of EtOAc, partitioned with 75 ml of DI water, and washed with 75 ml 1N HCl. The aqueous layer was extracted with 50 ml of EtOAc and the combined organic layers were washed with 2×75 ml of 1N HCl and 75 ml of brine. The organic layer was dried over MgSO₄, filtered, and concentrated under reduced pressure.

Preparation of D-Amphetamine Free Base:

D-amphetamine sulfate (0.7 g, 1.9 mmol) was taken up with 15 ml of MDC and partitioned with 10 ml of DI water.

The mixture was basified with 10% NaOH aq. solution to pH 9-10. The aqueous layer was extracted with 2×10 ml of MDC. The combined organic layers were dried over MgSO₄, filtered, and evaporated to dryness.

T3P Coupling of L-Lysine Free Acid with D-Amphetamine Free Base:

| Reagents | MW | Weight | mmoles | Molar Equivalents |
|---|---|---|---|---|
| Di-N-Boc-L-Lysine free acid | 346.42 | 1.3 g | 3.8 | 1.0 |
| D-amphetamine free base | 135.2 | 0.5 g | 3.8 | 1.0 |
| Diisopropylethylamine | 129.24 | 1.5 g | 11.4 | 3.0 |
| T3P (52.7% w/w) in EtOAc | — | 3.0 g | 4.9 | 1.3 |
| 1,4 Dioxane | — | 15 ml | — | — |

To a solution of Di-N-Boc-L-Lysine free acid (1.3 g, 3.8 mmol, 1 eq) in 10 ml EtOAc under N₂ was added DIPEA (1.5 g, 11.4 mmol, 3 eq) and the resulting mixture was allowed to stir at room temperature for 10 min. A solution of D-amphetamine free base (0.5 g, 3.8 mmol, 1 eq) in 5 ml EtOAc was added and the mixture stirred at ambient temperature for 20 min. T3P solution in EtOAc (52.7% w/w, 3.0 g, 4.9 mmol, 1.3 eq) was added slowly at 20-25° C. while cooling the flask externally with an ice/water bath. The reaction mixture was stirred for 1-2 hours at 20-25° C. which resulted in reaction completion. Upon reaction completion, 10 g of water were added while keeping the temperature <25° C. After mixing for 15 min, the aqueous layer was extracted with (2×10 ml) EtOAc. The combined organic phases were washed with saturated NaHCO₃ (2×15 ml) aqueous solution, and then 15 ml of brine. The organic layer was filtered and evaporated to dryness yielding the white solid Di-Boc-Lys-Amp.

Deprotection and Preparation of Mesylate Salt:

| Reagents | MW | Weight | mmoles | Molar Equivalents |
|---|---|---|---|---|
| Di-Boc-Lys-Amp | 463.62 | 1.76 g | 3.8 | 1.0 |
| Methanesulfonic Acid | 96.1 | 1.83 g | 19.0 | 5.0 |
| 1,4-Dioxane | — | 17.0 ml | — | — |

A 50 ml flask was charged with Di-Boc-Lys-Amp white solid, (1.76 g, 3.8 mmol, 1 eq) and 1,4-dioxane (15.0 ml) and the mixture was stirred rapidly under N₂ for 30 min. The resulting solution was filtered and the filter cake was rinsed with 1,4-dioxane (2×1.0 ml). To the combined filtrates (clear, slightly yellow solution) was added methanesulfonic acid (1.83 g, 19.0 mmol, 5 eq) over 1 hour while keeping the internal temperature at 21±3° C. Approximately 1 hour after the addition was completed, a white precipitate began to appear. The mixture was stirred at ambient temperature for 20.5 hours and until HPLC monitoring indicated the disappearance of all starting material. The slurry was filtered through filter paper and the flask was rinsed with 1.8 ml of 1,4-dioxane. The filter-cake was washed with 1,4-dioxane (3×1.8 mL) and then dried under vacuum at 55° C. for ~90 h. This afforded Lys-Amp dimesylate as a white solid.

Example 2

Synthesis of L-Lysine-d-Amphetamine Dimesylate

L-Lysine-d-Amphetamine was Synthesized by T3P Coupling of Di-Boc-L-Lysine Free Acid with d-Amphetamine Salt:

| Reagents | MW | Weight | mmoles | Molar Equivalents |
|---|---|---|---|---|
| Di-N-Boc-L-Lysine free acid | 346.42 | 1.3 g | 3.8 | 1.0 |
| D-amphetamine sulfate salt | 368.49 | 0.7 g | 3.8 | 1.0 |
| Diisopropylethylamine | 129.24 | 2.0 g | 15.2 | 4.0 |
| T3P (52.7% w/w) in EtOAc | — | 3.0 g | 4.9 | 1.3 |
| 1,4-Dioxane | — | 15 ml | — | — |

To 15 ml of EtOAc were added of Di-N-Boc-L-Lysine free acid (1.3 g, 3.8 mmol, 1 eq), DIPEA (2.0 g, 15.2 mmol, 4 eq), and the mixture was stirred at 20-25° C. for 10 min. D-amphetamine sulfate (0.7 g, 3.8 mmol, 1 eq), was added and the mixture stirred at 20-25° C. for 20 min. T3P solution in EtOAc, 52.7% w/w, (3.0 g, 4.9 mmol, 1.3 eq) was added slowly at 20-25° C. while cooling the flask externally with an ice/water bath. The reaction mixture then was stirred at 20-25° C. for 24 hour. After reaction completion 10 g of water were added at <25° C. (exothermic 2-3° C.) and mixed for 15 min. Two layers were separated and the aqueous layer was extracted with 5 g EtOAc. The combined organic phases were washed with saturated NaHCO₃ (15 ml) aqueous solution. The pH was adjusted to 8-9 using 10% NaOH. The organic phase was washed with DI water (10 ml) and then brine (10 ml). The organic solution was evaporated to dryness yielding the white solid Di-Boc-Lys-Amp.

Deprotection and Preparation of Mesylate Salt:

| Reagents | MW | Weight | mmoles | Molar Equivalents |
|---|---|---|---|---|
| Di-Boc-Lys-Amp | 463.62 | 1.76 g | 3.8 | 1.0 |
| Methanesulfonic Acid | 96.1 | 1.83 g | 19.0 | 5.0 |
| 1,4-Dioxane | — | 17.0 ml | — | — |

A 50 ml flask was charged with di-BOC-Lys-Amp white solid, (1.76 g, 3.8 mmol, 1 eq) and 1,4-dioxane (15.0 ml) and the mixture was stirred rapidly under N₂ for 30 min. The resulting solution was filtered and the filter cake was rinsed with 1,4-dioxane (2×1.0 ml). To the combined filtrates (clear, slightly yellow solution) was added methanesulfonic acid (1.83 g, 19.0 mmol, 5 eq) over 1 hour while keeping the internal temperature at 21±3° C. Approximately 1 hour after the addition was completed, a white precipitate began to appear. The mixture was stirred at ambient temperature for 20.5 hours and until HPLC monitoring showed the disappearance of all starting material. The slurry was filtered through filter paper, and the flask was rinsed with 1,4-dioxane (1.8 ml). The filter-cake was washed with 1,4-dioxane (3×1.8 ml) and then dried under vacuum at 55° C. for ~90 h. This afforded Lys-Amp dimesylate as a white solid, yield from Di-N-Boc-L-Lysine free acid 95%.

Comparison with Prior Art

The process according to the present invention was compared with the L-Lysine-D-amphetamine synthesis as described in WO/2006/121552. The following differences are noted:

1. WO '552 uses N$_\alpha$N$\epsilon$-Di-Boc-L-lysine hydroxysuccinimide ester as starting material, where the process according to this invention uses the free acid of N$_\alpha$N$_\epsilon$-Di-Boc-L-lysine (dicyclohexylammonium) salt. This means that one synthetic step starting from Lysine can be saved.
2. WO '552 uses 1.5 eq. of d-amphetamine when producing the mesylate salt, where the process according to this invention uses on 1.0 eq., reducing the total costs significantly.

3. WO '552 indicates a yield of approximately 91% in the coupling step whereas the process according to this invention achieves nearly quantitative conversions, further improving the economics of the process.

The invention claimed is:

1. A process for preparing acylated amphetamine, methamphetamine and dexamphetamine derivatives (V4 or V4a) or its salt comprising reacting a parent amine (V1) with a to be coupled acid (V2) or a salt of the to be coupled acid (V2), said acid (V2) further being optionally protected by protecting group(s)

in the presence of an alkylphosphonic acid anhydride (V3) as coupling agent and cleaving the protecting group(s) if the acid (V2) was protected, said process being performed in a one-pot reaction or in two or more separate steps according to the following equation 1:

EQUATION 1

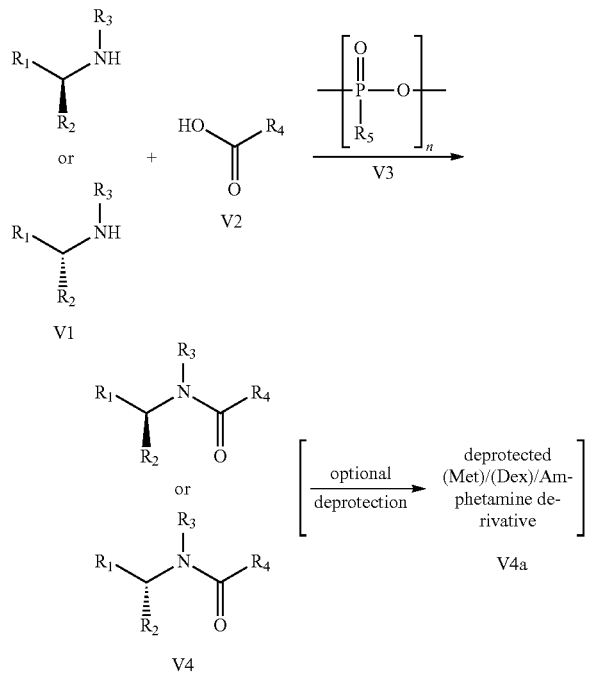

wherein n and the radicals R1 to R5 have the following meaning:

R1 is benzyl, mono-, di-, tri-lower-alkyl-substituted phenylmethyl, mono-, di- or tri-lower-alkoxy-substituted phenylmethyl, R2 is lower alkyl R3 is H or lower alkyl R4 is an amino acid radical or an amino acid radical wherein at least one amino group is protected with a protecting group, or is a substituted alkyl group different from the amino acid radical R5 is C1-C8-alkyl n is a number ranging from either 3 to 5 if (V3) is a cyclic anhydride or 3 to 1000 if (V3) is an open-chain oligomer, including if (V3) is a mixtures of different open-chain and/or cyclic anhydrides.

2. The process as claimed in claim 1, wherein the alkylphosphonic acid anhydride (V3) is a cyclic trimer of iso- and/or n-propylphosphonic acid anhydride or is an open-chain oligo- or polymer or is a mixture of cyclic and open-chain compounds.

3. The process as claimed in claim 1, wherein the alkylphosphonic acid anhydride (V3) is a cyclic trimer of n-propylphosphonic acid.

4. The process as claimed in claim 1, wherein the alkylphosphonic acid anhydride is optionally added in solution in a non-reactive solvent.

5. The process as claimed in claim 1, wherein said process is performed in a one-pot reaction.

6. The process as claimed in claim 1, wherein said process is performed in two or more separate steps.

7. The process as claimed in claim 1, said process further comprising performing the reaction at temperatures in the range of −20° C. to +80° C.

8. The process as claimed in claim 1, said process further comprising performing the reaction in the presence of a base.

9. The process as claimed in claim 1, wherein said process has a yield of >90%.

10. The process as claimed in claim 1, wherein (V4) or (V4a) has a purity of >98.0%.

11. The process as claimed in claim 1, wherein said process has an ee loss of <1.0%.

12. The process as claimed in claim 1, wherein (V4) or (V4a) is Lisdexamphetamine or a salt of Lisdexamphetamine, (V2) is N-protected Lysine and (V1) is Dexamphetamine.

* * * * *